United States Patent [19]

Blaschke et al.

[11] 4,415,488

[45] Nov. 15, 1983

[54] TRIAMINE-TRIOXIDES, A PROCESS FOR THEIR PREPARATION, AND CLEANING AGENTS CONTAINING THESE COMPOUNDS

[75] Inventors: Günter Blaschke, Winhöring; Alwin Reng, Kelkheim; Jochen M. Quack, Eppstein, all of Fed. Rep. of Germany

[73] Assignee: Hoechst Aktiengesellschaft, Fed. Rep. of Germany

[21] Appl. No.: 439,731

[22] Filed: Nov. 8, 1982

[30] Foreign Application Priority Data

Nov. 19, 1981 [DE] Fed. Rep. of Germany ....... 3145735

[51] Int. Cl.$^3$ .......................... C07C 79/16; C11D 1/75; C11D 7/32
[52] U.S. Cl. .................................... 252/547; 252/528; 252/DIG. 5; 564/297; 564/298; 568/704
[58] Field of Search ................. 252/547, 528, DIG. 5; 260/501.13; 564/294, 297, 298; 568/712, 704

[56] References Cited

U.S. PATENT DOCUMENTS 3,615,797 10/1971 Ohtsuka et al. .................... 106/278
3,819,539 5/1974 Bloch et al. ................ 260/501.13 X Primary Examiner—John E. Kittle
Assistant Examiner—Mukund J. Shah
Attorney, Agent, or Firm—Connolly and Hutz

[57] ABSTRACT

Triamine-trioxides of the formula

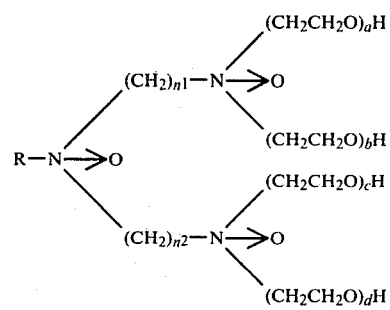

in which R denotes a saturated or an olefinically unsaturated hydrocarbon radical which has 1 to 3 double bonds and 8 to 22 carbon atoms, $n^1$ and $n^2$ represent an integer from 2 to 3, and $n^1$ and $n^2$ can be identical or different, and a, b, c and d, which are identical or different, each is a number from 1 to 5, with the proviso that the sum $(a+b+c+d)$ should be at most 10.

The compounds are prepared from primary amines of the formula $RNH_2$ by dicyanoalkylation, hydrogenation, ethoxylation and oxidation with hydrogen peroxide. They are suitable for formulating industrial and also cosmetic cleaning agents.

4 Claims, No Drawings

TRIAMINE-TRIOXIDES, A PROCESS FOR THEIR PREPARATION, AND CLEANING AGENTS CONTAINING THESE COMPOUNDS

The function of cosmetic and industrial cleaning agents is the removal of a very wide variety of contaminants from surfaces of organic or inorganic nature. The topography of surfaces to be cleaned varies considerably, also causing contaminants, such as pigments, oils, sebum or dust, to have differences in their adhesion.

In cleaning such soiled surfaces with aqueous surfactant solutions, both the necessary cleaning action and a specific, both quantitatively and qualitatively, foam appearance are required during the cleaning process. For most cleaning processes, the type and amount of this foam is an important indicator for how the cleaning step is proceeding with time. The consumer demands a foam appearance which is specific for the particular cleaning process especially in the case of cosmetic cleaning formulations, such as toothpastes, foam baths, shower baths, shampoos or soaps. The foam preferred in most of these cases consists of bubbles which are as fine as possible and is creamy and, at the same time, offers a number of advantages in the use of these cosmetic formulations. For example, a so-called foam blanket which is fine-bubbled and is dense acts in a thermally insulating manner when foam baths are used, i.e. the bathwater cools down at a considerably lower rate than the corresponding foam-free bathwater. When using a hair shampoo on the other hand, a very fine-bubbled foam structure which consists of bubbles as fine as possible prevents mechanical damage due to pulling or rubbing of the hair too severely; even in the case of toothpastes, a very dense foam appearance is desirable for protecting the gum during the brushing of the teeth. A similar point applies also to the use of foamy perming formulations. Finally, it is a wish of the consumer that when using body-cleaning agents, such as shower baths or hair shampoos, the foam is "triggered" as rapidly as possible, i.e. when the surfactant solution is subjected to a certain mechanical stress, for example rubbing with fingers, the maximum foam volume should be obtained in as short a time as possible.

Most of the surfactants which are customary in practice, such as alkyl sulfates, alkyl ether sulfates, alkylbenzenesulfonates, secondary alkanesulfonates, fatty alcohol polyglycol ethers and alkylphenols polyglycol ethers, produce on application in an aqueous solution a relatively coarse-bubbled foam, so that it is frequently necessary to include a third component, in addition to these surfactants and water, as a foam booster to stabilize the foam, since hand in hand with increasing particle size of the foam is an increasing collapse as a function of time.

A further disadvantage of such commercially available surfactants is their restricted possibility of use in the manufacture of industrial cleaning agents, such as cold cleaners, all-purpose cleaners, lavatory cleaners or washing-up liquids, for reasons of their physical and chemical stability. Thus, for example, alkyl sulfates, alkyl ether sulfates or sulfosuccinic acid half-esters can only be used in a neutral or alkaline medium, since hydrolytic cleavage with formation of sulfuric acid takes place in the acid pH range, which fact leads to the loss of the surface-active properties.

In contrast, nonionic surfactants, such as alkyl polyglycol ethers or alkylaryl polyglycol ethers, are decomposed in the strongly alkaline range. A further disadvantage of many surfactants is also their deficient stability in the presence of aqueous electrolytic solutions, since a physical salting-out effect takes place in the presence of silicates, phosphates or chlorides. Other surfactants are in turn decomposed in the presence of oxidizing agents.

There is therefore a need for surfactant-like substances which do not have the above disadvantages. Amine-oxides and diamine-dioxides, even those which have hydroxyethyl substituents, are known as surfactant-like substances which are said to be free of these disadvantages (cf., M. J. Schick "Nonionic Surfactants", Marcel Dekker, New York, 1967, page 403 et seq.; U.S. Pat. No. 3,197,509 and U.S. Pat. No. 3,234,139). However, these substances can satisfy the need only to a limited extent, since they lack adequate hydrophilic character and have unsatisfactory antistatic properties.

The invention now provides, for this purpose, triamine-trioxides of the general formula

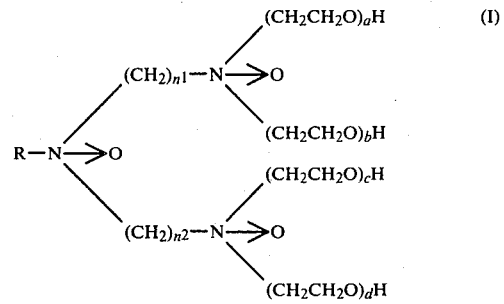

in which
R denotes a saturated or an olefinically unsaturated hydrocarbon radical which has 1 to 3 double bonds and 8 to 22 carbon atoms,
$n^1$ and $n^2$ represent an integer from 2 to 3, and $n^1$ and $n^2$ can be identical or different, and
a, b, c and d, which are identical or different, each is a number from 1 to 5, with the proviso that the sum (a+b+c+d) should be at most 10.

In these triamine-trioxides according to the invention, of the formula I, the radical R has 8 to 22 carbon atoms, it can be saturated or unsaturated with 1 to 3 olefinic double bonds, and it can be straight-chain or branched. These alkyl or alkenyl radicals, which originate in the primary starting amine in the preparation of triamine-trioxides according to the invention, are frequently mixtures or chain segments, preferably with the chain distribution of the radicals of natural fatty acids, such as, in particular, the coconut, tallow or palmitic fatty acid, from which these starting amines can be obtained via the path of nitrile-hydrogenation or ammonolysis of the corresponding alcohols. The alcohols used for preparing the primary amines by means of ammonolysis can be not only fatty alcohols but also those which have a straight or branched chain from the Ziegler process (alcohols obtained by the growth reaction from ethylene) or from the oxo synthesis.

To prepare compounds according to the invention, such a primary amine of the formula $RNH_2$ (II) in which R has the abovementioned meaning, is first reacted with 2 moles of at least one reactive nitrile of 2 to 3 carbon atoms (including the CN group) to give a compound of the general formula

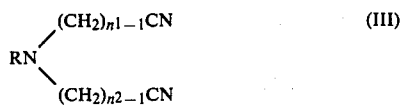

in a dicyanoalkylation reaction. This reaction is known, for example from U.S. Pat. No. 3,028,415. The reaction can be carried out not only with acidic but also with basic catalysis, with the aid of solvents, such as water or low-molecular weight alcohols, unpressurized or under an elevated pressure, in a continuous or discontinuous manner. Acidic catalysts mentioned are acetic acid, phosphoric acid, hydrochloric acid and other mineral acids (U.S. Pat. No. 3,615,797, U.S. Pat. No. 3,028,415 and German Offenlegungsschrift No. 1,941,913), and basic catalysts which have been recommended are sodium hydroxide, potassium hydroxide, alkali metal alcoholates, trimethylbenzylammonium hydroxide and morpholine (Kirk-Othmer, Encyclopedia of Chemical Technology, 1965, volume 6, page 634 et seq.; and H. A. Bruson "Cyanoethylation". Organic Reactions 5, 1949, page 79 et seq., published by John Wiley and Sons, New York). Water or lower alcohols, such as methanol, ethanol, isopropanol or mixtures of the same, are added as co-catalysts or also as solubilizers in amounts of 1 to 20% by weight. The dicyanoalkylation is carried out under atmospheric pressure or slight to medium overpressure of 1 to 20 bar, optionally in the presence of an inert gas, at temperatures of 60° to 150° C. The cyanoalkylating agent, preferably acrylonitrile or chloroacetonitrile, is used stoichiometrically or in up to four-fold excess.

The dicyanoalkylation product (III) thus obtained is then reduced in the presence of hydrogen to give a compound of the formula

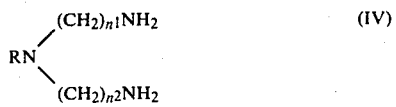

which is then condensed with ethylene oxide to give a compound of the formula

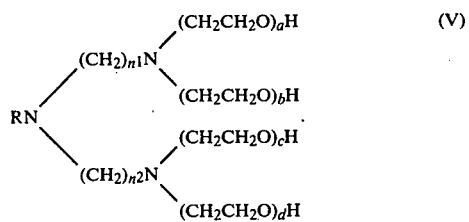

The two reactions to obtain the compounds at issue are also known (cf. the already-mentioned U.S. Pat. No. 3,615,797). The reduction is carried out by means of Raney nickel or Raney cobalt or by means of supported nickel or cobalt catalysts, namely with the use of 1 to 10% by weight of catalyst, preferably 1 to 5% by weight, under pressures of 50 to 200 bar of hydrogen and at temperatures of 60° to 150° C.; the time for this reaction is about 1 to 5 hours.

The ethoxylation reaction is carried out in pressure vessels, namely at an elevated temperature within a range of 110° to 170° C. and under an elevated pressure of 1 to 5 bar. A catalyst is not required if, preferably, only one ethylene oxide unit is to be added per chain. If a catalyst is used, ethylene oxide chains which contain more than one unit are preferentially obtained. 4 to 10 moles of ethylene oxide are used per 1 mole of compound IV in the reaction, preferably 4 to 5 moles. In the addition, the ethylene oxide can be diluted with an inert gas.

The ethylene oxide addition product thus obtained is then reacted in a way which is in itself known to give the triamine-trioxide according to the invention, and of the formula

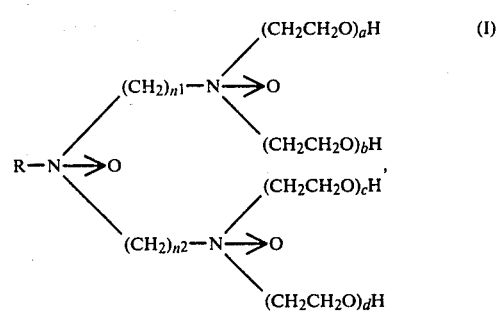

namely in an aqueous solution with 30 or 70% by weight strength of hydrogen peroxide. The reaction is carried out at 50° to 90° C. using a 5 to 10% excess of hydrogen peroxide, relative to the necessary amount of 3 moles.

Triamine-trioxides according to the invention, of the formula I, are advantageously prepared as 30 to 40% by weight strength aqueous formulations by suitably adjusting the water content in the final reaction stage.

Triamine-trioxides according to the invention are particularly suitable for preparing chemically and physically stable industrial and cosmetic cleaning agents. The particular characteristics of cleaning formulations prepared with these triamine-trioxides are a fine-bubbled foam, good foam-generating capacity and stability within a wide pH range. Further advantages are the physical stability in the presence of electrolytes, such as silicates, phosphates, bromates or the like, i.e. turbidities or precipitations, as occur in the case of many commercially available surfactants, do not arise in aqueous dilution. There is no chemical change even in the presence of oxidizing agents, such as hydrogen peroxide or chlorine bleaching liquor.

Triamine-trioxides according to the invention are particularly suitable for fomulating industrial cleaning agents, i.e. foam cleaners for textile areas, such as carpet cleaners, or, in particular, cleaning agents for hard surfaces, such as, for example, washing-up liquids, bottle-rinsing agents, floor cleaners, sanitary cleaners or so-called all-purpose cleaning agents.

Triamine-trioxides according to the invention, as defined in the abovementioned formula I, are also suitable for use in cosmetic cleaning agents, i.e. body-cleaning agents such as foam baths, shower baths, foot washes, hand washes or intim-sphere washes, and also in hair washes. On use in body-cleaning agents a marked improvement in the way the skin feels after the application is achieved, and on use in shampoos there is an improvement in the combability not only of dry but also of wet hair with a simultaneous softening effect, which manifests itself in the hair having a pleasant handle.

Triamine-trioxides according to the invention can be used in such liquid, pulverulent or aerosol-type industrial and cosmetic cleaning agents not only alone but also combined with anionic, cationic, nonionic and amphoteric surfactants which are customarily used in such agents. Examples of anionic surfactants which are suitable for this purpose are soaps, fatty alcohol sulfates, alkyl ether sulfates, fatty acid condensation products, such as taurides, methyltaurides and sarcosides, α-olefinsulfonates, hydroxyalkanesulfonates, secondary alkanesulfonates, amide ether sulfates and alkylbenzenesulfonates. Examples of compounds which can be used as nonionic surfactants are polyglycol monoalkyl ethers and monoesters, amine oxides and ethylene oxide/propylene oxide condensation products. In addition, the combination with other amphoteric surfactants, such as alkylbetaines, alkylamidobetaines, imidazoline derivatives or sulfobetaines, is also possible. Finally, triamine-trioxides according to the invention can also be used admixed with cationic surfactants, such as cetyltrimethylammonium chloride, cetyltrimethylammonium bromide, pentaoxyethylstearylammonium chloride, quaternized etheramines or polymeric quaternary ammonium compounds. Further additives which are used in an otherwise customary manner in cosmetic cleaning agents can be combined with the triamine-trioxides. Examples of these additives are viscosity-increasing or viscosity-decreasing compounds such as cellulose ethers, electrolytes, such as, for example, sodium chloride or ammonium chloride, fatty acid polyglycol esters, alkanolamides, magnesium aluminum silicates, polyglycols, glycerol and ethanol. Further additives which can be used are perfume oils and special fragrances, antiseptic agents, dandruff-removing or fungus-killing agents, superfatting agents, preservatives, dyestuffs and nacreous substances. Filler and carrier substances which are customarily used, such as highly disperse and amorphous silica, sodium sulfate, magnesium aluminum silicate, starch derivatives and the like, can also be used in the processing to give pulverulent formulations. Finally, customary propellant gases can also be admixed in the case of aerosol-type formulations. To control the pH value desired, inorganic or organic acids or alkalis can be used. Chelating agents and, if appropriate, also dispersions of plastics can be added as customary auxiliaries to industrial cleaning agents. Other additives which are customary for this purpose are bleaching agents, chlorine-donors or other disinfectants. To improve the abrasion effect, suitable additives are chalk, highly disperse amorphous silica, phosphates and plastics. To improve the fat- and soil-solubilizing properties, solvents such as universal spirit or isopropyl alcohol or other cleaning-promoting agents can also be added. Finally, the triamine-trioxides according to the invention are suitable for use as agents for washing textiles.

The content of triamine-trioxides according to the invention in such formulations is usually 0.5 to 40% by weight.

The examples which follow are intended to illustrate the invention in more detail:

PREPARATION EXAMPLES

EXAMPLE 1

670 g of coconut fatty amine (mole % composition in respect of the R radicals: $C_8$ 6%, $C_{10}$ 6%, $C_{12}$ 54%, $C_{14}$ 18%, $C_{16}$ 8% and $C_{18}$ 8%), 68 g of water, 34 g of methanol and 14 g of concentrated acetic acid were heated to 60° C. in a 2 liter four-necked flask equipped with a refulx condenser, thermometer, stirrer and metering vessel. 373 g of acrylonitrile were added dropwise in the course of one hour, and the mixture was stirred for a further 24 to 36 hours at 75° C. under reflux. The mixture was then neutralized with 13 g of NaOH and 120 g of water, the wash water was separated off, and the product was freed from residual water and solvent in vacuo. 1,000 g of coconut-aminodipropionitrile (yield: 95.9%) were obtained.

A 5 liter autoclave was filled with 2,020 g of coconut-aminodipropionitrile, 3 g of supported cobalt catalyst (support: kieselguhr) and 300 ml of liquid ammonia. The hydrogenation took 3 hours under 150 to 180 bar of $H_2$ and at 110° to 140° C. After the catalyst had been filtered off, 2,010 g of a product which contained 85 to 95% of bis-(3-aminopropyl)-coconut-amine were obtained.

954 g of bis-(3-aminopropyl)-coconut-amine were heated with stirring to 130° C. in a 2 liter pressure vessel equipped with a thermometer, stirrer and an inlet and outlet for ethylene oxide. 667 g of ethylene oxide were added under a pressure of 1 to 3 bar. The increase in weight after a reaction time of 3 hours corresponded to a condensation product of the triamine with 4 to 5 moles of ethylene oxide. 1,605 g of this ethoxylate (99%) were obtained.

261 g of bis-(3-aminopropyl)-coconut-aminoethoxylate and 559 g of water were initially introduced into a 2 liter reaction vessel and heated with stirring to 60° C. 146 g of 70% by weight strength hydrogen peroxide were added at this temperature within 1 hour, and the mixture was stirred for a further 12 hours at 60° C. The corresponding triamine-trioxide was obtained in 960 g of a 30% by weight strength aqueous solution.

EXAMPLE 2

670 g of laurylamine ($C_{12}$-fraction: 73 mole %, and $C_{14}$-fraction: 23 mole %) were reacted in the manner already described in Example 1 with 373 g of acrylonitrile in 68 g of water, 34 g of methanol and 14 g of concentrated acetic acid, and the product was then hydrogenated. 2,020 g of bis-(3-aminopropyl)-laurylamine were obtained after the hydrogenation. 954 g of this triamine were condensed with 640 g of ethylene oxide. 1,590 g of bis-(3-aminopropyl)-laurylamine ethoxylate (99%) were obtained. 257 g of this ethoxylate and 538 g of water were reacted with 146 g of 70% by weight strength $H_2O_2$. The triamine-trioxide was obtained in 935 g of a 30% by weight strength aqueous solution.

EXAMPLE 3

844 g of myristylamine were reacted at 75° C. with 373 g of acrylonitrile in 68 g of water, 34 g of methanol and 14 g of concentrated acetic acid. 1,164 g of myristylaminodipropionitrile were obtained. 2,052 g of the dipropionitrile were hydrogenated in the manner of Example 1 using a cobalt catalyst. 2,045 g of bis-(3-aminopropyl)-myristylamine were obtained. 1,095 g of this triamine were condensed with 647 g of ethylene oxide. 1,725 g of bis-(3-aminopropyl)-myristylamine ethoxylate (99%) wereobtained. 290 g of this ethoxylate and 615 g of water were reacted with 146 g of 70% by weight strength $H_2O_2$. The triamine-trioxide was obtained in 1,050 g of a 30% by weight strength aqueous solution.

EXAMPLE 4

1,056.0 g of octylamine were reacted at 75° C. with 849.6 g of acrylonitrile in 106 g of water, 53 g of methanol and 21.1 g of concentrated acetic acid. 1,810 g of octylaminodipropionitrile were obtained. 1,980 g of the dipropionitrile were hydrogenated in the manner of Example 1 using a cobalt catalyst. 1,970 g of bis-(3-aminopropyl)-octylamine were obtained. 998 g of this triamine were condensed with 845 g of ethylene oxide. 1,840 g of bis-(3-aminopropyl)-octylamine ethoxylate (99%) were obtained. 230 g of this ethoxylate and 475 g of water were reacted with 146 g of 70% by weight strength $H_2O_2$. The triamine-trioxide was obtained in 850 g of a 30% by weight strength aqueous solution.

EXAMPLE 5

929 g of tallow fatty amine were reacted at 75° C. with 373 g of acrylonitrile in 68 g of water, 34 g of methanol and 14 g of concentrated acetic acid. 1,237 g of tallow-fatty-aminodipropionitrile were obtained and hydrogenated in accordance with Example 1 to give the corresponding amine. 1,230 g of bis-(3-aminopropyl)-tallow-fatty-amine were obtained. The ethoxylation reaction was carried out in two stages. First, 1,154 g of bis-(3-aminopropyl)-tallow-fatty-amine were reacted with 647 g (4.7 moles) of ethylene oxide using the method of Example 1. The product was then reacted with a further 5.3 moles of ethylene oxide in the presence of the customary 0.2% by weight, relative to the amine, of aqueous sodium hydroxide solution (50% strength), so that the total increase in weight corresponded to a condensation product of the triamine with 10 moles of ethylene oxide. 300 g of this ethoxylate and 639 g of water were reacted with 146 g of 70% by weight strength $H_2O_2$. The triamine-trioxide was obtained in 1,020 g of a 30% by weight strength aqueous solution.

The analytical data of the triamine-trioxides according to the invention, and of their precursors, are summarized in Table I.

in isopropanol in an anhydrous medium. The distribution of amine is carried out by blocking the basic amine-nitrogen with salicylaldehyde (primary N) and phenyl isothiocyanate (primary and secondary N) respectively.

Ethoxylate

The amine number and the tertiary nitrogen content are determined by titration with 0.1 N $HClO_4$ in glacial acetic acid or acetic anhydride. The moles of ethylene oxide absorbed are calculated from the amine numbers or from the increase in mass compared to the previous stage.

Triamine-trioxide

The amine number is determined by titration with 0.2 N solution of HCl in isopropanol in an anhydrous medium. The triamine-trioxide content is determined by redox titration with titanium(III) chloride/$NH_4Fe(SO_4)_2 \cdot 6H_2O$.

The application examples which follow illustrate the ways triamine-trioxides can be used in industrial and cosmetic cleaning agents, even in special formulations, such as shaving soaps, perming formulations or other products where not only foam properties but particularly chemical and physical stability are required.

EXAMPLE 1 A

Acidic cleaning agent

Triamine-trioxide of the formula I, prepared according to Example 1—5.0%
Orthophosphoric acid—30.0%
Water—to 100.0%

EXAMPLE 2 A

Disinfecting cleaner

Triamine-trioxide of the formula I, prepared according to Example 2—5.0%
Lauryldimethylbenzylammonium chloride—5.0%
Citric acid—0.2%
Water—to 100.0%

TABLE I

| Example/ (alkyl radical) | Alkylamino-dipropio-nitrile | | Bis-(3-aminopropyl)-alkylamine | | | | Ethoxylate | | Σa + b + c + d Equivalents of EO+ per mole | Triamine-trioxide Content | |
|---|---|---|---|---|---|---|---|---|---|---|---|
| | AN | Tert. N (%) | AN | Prim. N (%) | Sec. N (%) | Tert. N (%) | AN | Tert. N (%) | | AN | % by weight |
| 1 (coconut) | 34.3 | 94 | 97.3 | 66.2 | 3.3 | 30.5 | 57.5 | >98 | 4.9 | 15.8 | 29.5 |
| 2 (lauryl) | 34.4 | 95 | 97.5 | 65.9 | 2.9 | 31.2 | 58.3 | >98 | 4.7 | 16.0 | 30.0 |
| 3 (myristyl) | 29.2 | 94 | 82.2 | 65.5 | 3.5 | 31.0 | 51.7 | >98 | 4.9 | 14.0 | 29.4 |
| 4 (octyl) | 42.7 | 94 | 120.2 | 65.1 | 3.0 | 31.9 | 65.1 | >98 | 4.8 | 17.5 | 29.7 |
| 5 (tallow fat) | 27.4 | 94 | 78.0 | 66.1 | 2.6 | 31.3 | 50.0 | >98 | 4.9 | 13.6 | 29.5 |

+EO = ethylene oxide

The abovementioned data are determined as follows:

Alkylaminodipropionitrile

The amine number (AN) and the tertiary nitrogen content are determined by titration with 0.1 N $HClO_4$ in glacial acetic acid or acetic anhydride. The amine number is given by $$AN = \frac{\text{ml of 0.1 N } HClO_4}{\text{original sample weight in g}}$$

Bis-(3-aminopropyl)-alkylamine

The amine number and the distribution of the amine are determined by titration with 0.2 N solution of HCl

EXAMPLE 3 A

Synthetic soap

Triamine-trioxide of the formula I, prepared according to Example 1—5.0%
Sodium salt of coconut-isothionate—60.0%
Stearic acid—10.0%
Titanium dioxide—2.0%
Cetyl alcohol—to 100.0%

EXAMPLE 4 A

Universal washing paste

Triamine-trioxide of the formula I, prepared according to Example 1—10.0%
Sodium salt of secondary alkanesulfonate ($C_{13}$–$C_{17}$)—15.0%
Sodium tripolyphosphate—3.0%
Sodium chloride—5.0%
Carboxymethylcellulose—5.0%
Water, preservatives—to 100.0%

EXAMPLE 5 A

All-purpose cleaner

Triamine-trioxide of the formula I, prepared according to Example 1—10.0%
Nonylphenol condensed with 10 moles of ethylene oxide—3.0%
Coconut fatty acid monoethanolamide condensed with 5 moles of ethylene oxide—2.0%
Tetrapotassium pyrophosphate—6.0%
Water, dyestuff, perfume oil, preservative—to 100.0%

EXAMPLE 6 A

Floor cleaner

Triamine-trioxide of the formula I, prepared according to Example 1—7.0%
Sodium tripolyphosphate—5.0%
Potassium hydroxide—1.5%
Water, perfume oil—to 100.0%

EXAMPLE 7 A

Grill cleaner

Triamine-trioxide of the formula I, prepared according to Example 1—15.0%
Nonylphenol condensed with 6 moles of ethylene oxide—8.0%
Stearic acid—1.0%
Sodium hydroxide—10.0%
Calcium carbonate—20.0%
Water, preservative—to 100.0%

EXAMPLE 8 A

Sanitary cleaner

Triamine-trioxide of the formula I, prepared according to Example 2—10.0%
Sodium salt of dodecylbenzenesulfonate—5.0%
Isopropanol—5.0%
Orthophosphoric acid—8.0%
Water, disinfectant—to 100.0%

EXAMPLE 9 A

Lavatory cleaner

Triamine-trioxide of the formula I, prepared according to Example 1—5.0%
α-Olefinsulfonate ($C_{14}$–$C_{16}$)—2.0%
Nonylphenol condensed with 8 moles of ethylene oxide—2.0%
Orthophosphoric acid—10.0%
Butylglycol—5.0%
Water—to 100.0%

EXAMPLE 10 A

Light-duty detergent

Triamine-trioxide of the formula I, prepared according to Example 2—10.0%
Sodium salt of lauryltriglycol ether sulfate—2.0%
Isotridecyl alcohol condensed with 8 moles of ethylene oxide—2.0%
p-Toluenesulfonate—4.0%
Tetrapotassium pyrophosphate—12.0%
Sodium tripolyphosphate—4.0%
Water, preservative, perfume oil—to 100.0%

EXAMPLE 11 A

High-pressure cleaner

Triamine-trioxide of the formula I, prepared according to Example 2—5.0%
Octanephosphonic acid—3.0%
Sodium tripolyphosphate—10.0%
Potassium hydroxide—3.0%
Sodium metasilicate x $5H_2O$—10.0%
Ethylenediamine condensed with 30 moles of ethylene oxide and 60 moles of propylene oxide—2.0%
Water—to 100.0%

EXAMPLE 12 A

Sanitary cleaner

Triamine-trioxide of the formula I, prepared according to Example 2—5.0%
Sodium salt of secondary alkanesulfonate (alkane radical: $C_{13}$–$C_{17}$)—2.0%
Sodium hydroxide—0.5%
Sodium hypochlorite solution (150 g of active chlorine/l)—50.0%
Water, perfume oil—to 100.0%

Example 13 A

Liquid detergent

Triamine-trioxide of the formula I, prepared according to Example 2—15.0%
Potassium soap (40% strength)—10.0%
Octanephosphonic acid—5.0%
Potassium hydroxide—3.0%
Potassium tripolyphosphate (50% strength)—30.0%
Sodium metasilicate—5.0%
Water, preservative, optical brightener, perfume oil—to 100.0%

EXAMPLE 14 A

Chalk cleaner

Triamine-trioxide of the formula I, prepared according to Example 2—8.0%
Nonylphenol condensed with 8 moles of ethylene oxide—1.0%
Lauryl alcohol—1.5%
Tetrasodium pyrophosphate—3.0%
Chalk—40.0%
Water, perfume oil, formalin—to 100.0%

EXAMPLE 15 A

Hair shampoo

Triamine-trioxide of the formula I, prepared according to Example 1—15.0%
Perfume oil—0.2%
Citric acid—0.3%

EXAMPLE 16 A

Hair shampoo for greasy hair

Triamine-trioxide of the formula I, prepared according to Example 2—5.0%
Sodium salt of lauryldiglycol ether sulfate—10.0%
Perfume oil—0.1%
Water, preservative—to 100.0%

EXAMPLE 17 A

Shower bath

Triamine-trioxide of the formula I, prepared according to Example 1—10.0%
Disodium salt of coconut-triglycol ether sulfosuccinate—5.0%
Coconut-fatty acid monoethanolamide—1.0%
Water, preservative, perfume oil—to 100.0%

EXAMPLE 18 A

Foam bath

Triamine-trioxide of the formula I, prepared according to Example 2—20.0%
Triethanolamine salt of lauryl sulfate—5.0%
Sodium salt of secondary alkanesulfonate ($C_{13}$-$C_{17}$)—5.0%
Oleic acid ethanolamide—2.0%
Hydroxyethylcellulose ether—1.3%
Water, preservative, perfume oil—to 100.0%

EXAMPLE 19 A

Baby shampoo

Triamine-trioxide of the formula I, prepared according to Example 2—10.0%
Sodium salt of lauroyl sarcoside—3.0%
Citric acid—0.2%
Water, preservative, dyestuff, consistency regulator, perfume oil—to 100.0%

EXAMPLE 20 A

Hand wash

Triamine-trioxide of the formula I, prepared according to Example 1—10.0%
α-Olefinsulfonate ($C_{14}$-$C_{16}$)—3.0%
Coconut-fatty acid diethanolamide—2.0%
Triethylene glycol distearate—1.0%
Water, consistency regulator, preservative, dyestuff—to 100.0%

EXAMPLE 21 A

Conditioning shampoo

Triamine-trioxide of the formula I, prepared according to Example 1—10.0%
Coconut-betain—3.0%
Cetyltrimethylammonium chloride—1.0%
Citric acid—0.2%
Water, consistency regulator, dyestuff—to 100.0%

EXAMPLE 22 A

Anti-dandruff shampoo

Triamine-trioxide of the formula I, prepared according to Example 1—12.0%
Sodium salt of coconut-fatty acid methyl tauride—5.0%
Trioctaglycol ether orthophosphoric acid ester—1.0%
Zinc pyrithione—1.0%
Water, preservative, consistency regulator, dyestuff—to 100.0%

EXAMPLE 23 A

Hair-smoothing agent

Triamine-trioxide of the formula I, prepared according to Example 2—1.0%
Sodium hydroxide—2.0%
Tragacanth—2.0%
Cetyl alcohol—3.0%
Water—to 100.0%

EXAMPLE 24 A

Hair conditioner

Triamine-trioxide of the formula I, prepared according to Example 1—1.0%
Distearyldimethylammonium chloride—3.0%
Stearylpentaoxyethylammonium chloride—1.0%
Cetylstearyl alcohol—3.0%
Water, dyestuff, perfume oil—to 100.0%

EXAMPLE 25 A

Hair dye

Triamine-trioxide of the formula I, prepared according to Example 2—0.5%
p-Toluidinediamine—1.0%
Resorcinol—1.0%
Cetylstearyl alcohol—8.0%
Ammonia—1.0%
Sodium sulfite—0.1%
Water—to 100.0%

EXAMPLE 26 A

Perm-setting agent

Triamine-trioxide of the formula I, prepared according to Example 2—2.0%
Hydrogen peroxide—2.0%
Citric acid—0.4%
Water, perfume oil, stabilizer—to 100.0%

EXAMPLE 27 A

Shaving soap

Triamine-trioxide of the formula I, prepared according to Example 1—3.0%
Myristic acid—10.0%
Stearic acid—23.0%
Coconut fatty acid—6.0%
Potassium hydroxide—7.0%
Sodium hydroxide—0.5%
Triethanolamine—1.0%
Water, perfume oil—to 100.0%

EXAMPLE 28 A

Toothpaste

Triamine-trioxide of the formula I, prepared according to Example 2—1.5%
Dicalcium phosphate—35.0%
Calcium carbonate—10.0%
Glycerol—5.0%
Hydroxyethylcellulose ether—2.0%
Saccharin—0.1%
Sodium fluoromonophosphate—0.76%
Water, aromatic oil, preservative—to 100.0%

EXAMPLES 29 A

Washing-up liquid

Triamine-trioxide of the formula I, prepared according to Example 1—10.0%
Sodium salt of secondary alkanesulfonate (alkane radical: $C_{13}$–$C_{17}$)—20.0%
Sodium tripolyphosphate—1.0%
Ethanol—3.0%
Water—to 100.0%

Tables Ia and Ib demonstrate the excellent foam stability, i.e. the stability of the foam as a function of time, in a comparison of triamine-trioxides according to the invention with the sodium salt of lauryl sulfate (Ia) and a secondary alkanesulfonate (chain segment: $C_{13}$–$C_{17}$) (Ib) and with their mixture with the compound according to the invention in a ratio of 1:1. The foam behavior was determined using the perforated-plate beating method in accordane with DIN standard 53,902; in this method, the foam is generated by beating an aqueous surfactant solution in a graduated measuring cylinder with the aid of a perforated plate and the height of the foam is read off visually at certain time intervals.

TABLE Ia

Foam height in ml
Concentration: 0.2% of active ingredient
Temperature: 40° C.
Water hardness: 20° of German hardness

| Time | Sodium salt of lauryl sulfate | Triamine-trioxide of Preparation Example 1 | 1:1 mixture |
|---|---|---|---|
| immediately | 400 | 700 | 570 |
| 5 min | 360 | 680 | 560 |
| 10 min | 300 | 630 | 530 |
| 15 min | 280 | 600 | 510 |
| 20 min | 200 | 480 | 500 |
| 25 min | 140 | 370 | 480 |
| 30 min | 80 | 270 | 460 |

TABLE Ib

| Time | Secondary alkanesulfonate | Triamine-trioxide of Preparation Example 1 | 1:1 mixture |
|---|---|---|---|
| immediately | 310 | 700 | 580 |
| 5 min | 280 | 680 | 550 |
| 10 min | 210 | 630 | 510 |
| 15 min | 200 | 600 | 420 |
| 20 min | 170 | 480 | 400 |
| 25 min | 120 | 370 | 380 |
| 30 min | 80 | 270 | 250 |

To determine the so-called foaming-up capacity as well as the water retention capacity of the foams, the rubbing foam method of Wilmsmann, Fette-Seifen-Anstrichmittel 66, 955 (1964) was used. In this method, the foam is generated for 5 minutes with the aid of a rotating plastic brush and the foam water separated off is then determined, also within 5 minutes. The corresponding results are shown in Table II, in a comparison with the sodium salt of lauryl sulfate.

TABLE II

Foam volume in ml
Concentration: 0.2% of active ingredient
Temperature: 40° C.
Water hardness: 20° German hardness

| | Time | Triamine-trioxide of Preparation Example 1 | Sodium salt of lauryl sulfate |
|---|---|---|---|
| Foam development | 30 sec | 1,200 | 1,150 |
| | 1 min | 1,230 | 1,170 |
| | 2 min | 1,330 | 1,250 |
| | 3 min | 1,410 | 1,300 |
| | 4 min | 1,470 | 1,360 |
| | 5 min | 1,500 | 1,430 |
| Foam stability | 0 min | 1,500 | 1,430 |
| | 1 min | 1,400 | 1,350 |
| | 2 min | 1,340 | 1,280 |
| | 3 min | 1,280 | 1,250 |
| | 4 min | 1,250 | 1,170 |
| | 5 min | 1,200 | 1,100 |

A further advantage of triamine-trioxides according to the invention is the stability even in the acid pH range; corresponding values were measured by storing the substances for 10 weeks in 20% by weight strength concentration in water at +40° C. and measuring the pH value at regular intervals. Table III shows that the triamine-trioxide according to the invention, unlike the hydrolysis-sensitive alkyl ether sulfate, does not show a drop in the pH value.

TABLE III pH stability at 40° C.

| Time | Triamine-trioxide of Preparation Example 1 | Sodium salt of lauryldiglycol ether sulfate |
|---|---|---|
| immediately | 7.7 | 7.6 |
| 1 week | 7.7 | 7.0 |
| 2 weeks | 7.8 | 5.8 |
| 3 weeks | 7.9 | 4.6 |
| 4 weeks | 8.0 | 4.0 |
| 5 weeks | 8.0 | 3.7 |
| 6 weeks | 8.0 | 3.5 |
| 7 weeks | 8.0 | 3.4 |
| 8 weeks | 8.0 | 3.4 |
| 9 weeks | 8.0 | 3.4 |
| 10 weeks | 8.0 | 3.4 |

We claim:
1. A triamine-trioxide of the formula

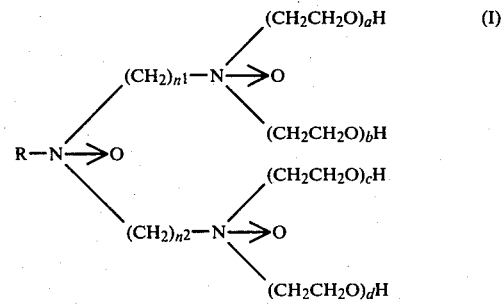

in which
R denotes a saturated or an olefinically unsaturated hydrocarbon radical which has 1 to 3 double bonds and 8 to 22 carbon atoms,
$n^1$ and $n^2$ represent an integer from 2 to 3, and $n^1$ and $n^2$ can be identical or different, and a, b, c and d, which are identical or different, each is a number from 1 to 5, with the proviso that the sum (a+b+c+d) should be at most 10.

2. A process for preparing a triamine-trioxide as claimed in claim 1, in which, first, a primary amine of the formula $RNH_2$ (II) is reacted with 2 moles of at least one reactive nitrile of 2 to 3 carbon atoms to give a compound of the formula

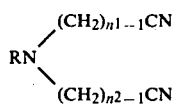 (III)

which is reduced in the presence of hydrogen to give a compound of the formula

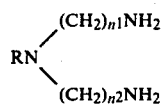 (IV)

which is condensed with ethylene oxide to give a compound of the formula

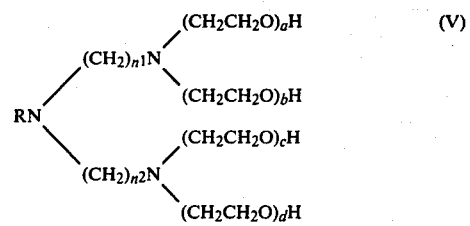 (V)

which process comprises oxidizing this compound of the formula (V) in an aqueous solution with hydrogen peroxide.

3. An industrial cleaning agent, containing water as a liquid carrier, at least one surfactant from the group consisting of anionic, cationic, nonionic and amphoteric surfactants and, cleaning-promoting additives and customary auxiliaries, which comprises a surface active effective amount of a triamine-trioxide as claimed in claim 1.

4. A cosmetic cleaning agent, containing water as a liquid carrier, at least one surfactant from the group consisting of anionic, cationic, nonionic and amphoteric surfactants, customary cosmetic additives and auxiliaries, which comprises a surface active effective amount of a triamine-trioxide as claimed in claim 1.

* * * * *